United States Patent [19]

Mawhirt et al.

[11] Patent Number: 4,944,924

[45] Date of Patent: * Jul. 31, 1990

[54] TEST TUBE HOLDER

[75] Inventors: James A. Mawhirt, Brooklyn; Joseph E. DiFlora, Eastchester, both of N.Y.; William J. C. McCandless, Ringwood, N.J.; George H. Ward, So. Ozone Park, N.Y.

[73] Assignee: Technicon Instruments Corporation, Tarrytown, N.Y.

[*] Notice: The portion of the term of this patent subsequent to Aug. 29, 2006 has been disclaimed.

[21] Appl. No.: 61,252

[22] Filed: Jun. 11, 1987

[51] Int. Cl.[5] .................................................. B01L 9/06
[52] U.S. Cl. ........................................ 422/104; 422/65; 422/100; 422/102; 220/23.4; 220/23.83; 220/23.86; 206/446; 206/558; 206/559; 206/560; 211/71; 211/74
[58] Field of Search .................. 422/65, 100, 102, 104; 220/23.4, 23.8, 23.83, 23.86; 206/446, 558, 559, 560; 211/71, 74

[56] References Cited

U.S. PATENT DOCUMENTS

| | | | |
|---|---|---|---|
| 3,186,556 | 6/1965 | Forsstrom | 211/74 |
| 3,350,946 | 11/1967 | Isreeli | 422/67 X |
| 3,521,785 | 7/1970 | Bergmann et al. | 220/23.4 |
| 3,538,962 | 11/1970 | Gilson | 220/23.4 X |
| 4,295,601 | 10/1981 | Cowell | 211/74 X |
| 4,301,964 | 11/1981 | Cowell | 211/74 X |
| 4,472,357 | 9/1984 | Levy et al. | 422/102 |
| 4,609,017 | 9/1986 | Coulter et al. | 422/65 X |
| 4,685,565 | 8/1987 | Sparling | 220/23.4 X |
| 4,815,625 | 3/1989 | Filhol et al. | 422/102 X |
| 4,861,553 | 8/1989 | Mawhirt et al. | 422/65 |

Primary Examiner—Robert J. Warden
Assistant Examiner—Lynn M. Kummert
Attorney, Agent, or Firm—Jeffrey M. Greenman

[57] ABSTRACT

The test tube holder includes an elongated tubular member which supports a pivot member thereby rendering the tubular member and pivot member relatively pivotable with respect to each other. Latch members provided on the tubular member and pivot member are engagable with complementary shaped latch members of other test tube holders to form a linkage. The pivotal relationship between the tubular member and the pivot member permit pivotal movement of one test tube holder with respect to the longitudinal axis of another test tube holder. A pivotal connection between the latch members of adjacent test tube holders also permits tilting of one test tube holder with respect to another test tube holder in the linkage. An adapter member for holding test tubes is insertable in the tubular member and pivot member assembly. The adapter member accommodates one size test tube and can be interchanged with another adapter member that accommodates another size test tube. Thus, the linkage of test tube holders can include test tubes of different size. The relative pivotal movement between test tube holders in the linkage permits stacking of the linkage in a fan-fold arrangement. The tilting movement between test tube holders in a linkage permits mixing of the contents of a test tube or a group of test tubes independent of all others in the linkage before a sample is tested. Under this arrangement, a linkage of test tubes of unlimited length can be provided.

38 Claims, 5 Drawing Sheets

TEST TUBE HOLDER

SUMMARY OF THE INVENTION

This invention relates to test tube holders, and more particularly to a test tube holder which can be linked together with other similar test tube holders in continuous fashion in a manner which permits relative pivoting and tilting of the test tube holders.

It is well known to analyze body fluids such as blood in an apparatus that automatically performs one or more desired tests on a sample of the fluid. Generally, the fluid samples are contained in a sealed test tube.

In some instances, an operator or technician transfers individual test tubes to the test apparatus. In other instances, the apparatus is adapted to receive plural quantities of test tubes such as shown in U.S. Pat. No. 4,609,017.

The apparatus of U.S. Pat. No. 4,609,017 receives test tubes in a batch feed arrangement wherein racks of test tubes are delivered into the apparatus. A disadvantage of the batch feed arrangement is that the test tubes must be mounted in special cassettes which are manually installed in the apparatus. A further disadvantage is that after the test is completed, the operator must manually remove the cassettes from the apparatus. Thus there is no disclosure of a continuous feed arrangement for feeding thest tubes to a sampling station of the test apparatus.

A prior approach to feeding sample containers to a sampling station of a test apparatus, as shown in U.S. Pat. No. 3,350,946, requires provision of a mounting boss on the test tube. The mounting boss engages a complementary shaped recess fixed to the periphery of a feed disc. The disclosed feed arrangement is not adaptable to disposable test tubes because of the expense of incorporating a mounting boss on the test tubes. In addition, this arrangement has no provision for pivoting or tilting of individual test tubes, which is often necessary to insure that a sample is properly mixed when it reaches the sampling station of the test apparatus.

Another known holding device for test tubes as shown in U.S. Pat. No. 3,521,785 is connected together in chain-like fashion by using the test tubes to form the joints of the chain. Removal or breakage of one test tube will cause a break in the chain. In addition, this device does not permit relative tilting between consecutive test tubes for mixing of samples that are in proximity of a sampling station of the test apparatus.

It is thus desirable to provide a test tube holder which can be easily linked together with other test tube holders to form a continuous linkage, and wherein the connection between each test tube holder permits tilting of one holder with respect to another to provide a mixing action. It is also desirable that the linkage of test tube holders be sufficiently flexible to permit stacking of the test tube holders in a fan-fold arrangement.

OBJECTS AND SUMMARY OF THE INVENTION

Among the several objects of the invention may be noted the provision of a novel test tube holder, a novel test tube holder which accomodates test tubes of varying size, a novel test tube holder which can be connected to other similar test tube holders in a continuous linkage wherein any one of the test tube holders can be pivoted about a longitudinal axis of another test tube holder in the linkage, a novel test tube holder which can be connected to other similar test tube holders in a continuous linkage wherein any one of the test tube holders in the linkage can be tilted with respect to the other test tube holders, a novel test tube holder which permits easy insertion and removal of a test tube from the holder, and a novel method of holding test tubes.

Other objects and features of the invention will be in part apparent and in part pointed out hereinafter.

In accordance with the present invention, the test tube holder includes an elongated tubular member provided with a pivot member pivotably supported on the elongated tubular member for pivotal movement about a longitudinal axis of the tubular member. Latch members are respectively provided on the tubular member and the pivot member. The pivotal mounting of the pivot member on the tubular member permits relative pivotal movement between the tubular member and the pivot member. Under this arrangement the latch members are relatively moveable toward and away from each other in a radial direction.

An adapter member for holding test tubes is insertable in the elongated tubular member and in the inserted position is embraced by the pivot member. A test tube is insertable in and removable from the adapter member and different adapter members can be interchanged to hold different size test tubes.

A plurality of test tube holders is linked together whereby the latch member provided on the tubular member of one test tube holder engages the latch member provided on the pivot member of another test tube holder. The pivotal relationship between the tubular member and the pivot member enables one test tube holder to pivot about the longitudinal axis of another test tube holder. The range of pivotal movement is sufficient to permit stacking of the test tube holders in a linkage, in a fan-fold or Z-fold arrangement.

The latch arrangement also forms a pivot joint between adjacent test tube holders in the linkage. Thus, the test tube holders are further moveable with respect to each other in a manner whereby the longitudinal axis of one test tube holder can be tilted about the pivot joint of the latch members in a skewed relationship with respect to the longitudinal axis of another test tube holder. Under this arrangement, one or more test tube holders in the linkage can be tilted with respect to other test tube holders in the linkage to provide a mixing action for the contents of the test tube.

Axial slots provided in the tubular member and the adapter member render such members expandable and resilient to releasably hold each other as well as the test tube which is received in the adapter member.

Under this arrangement test tubes are easily inserted in and removed from the test tube holders and different adapter members are interchangeable to permit the test tube holder to hold different size test tubes.

The invention accordingly comprises the constructions and method hereinafter described, the scope of the invention being indicated in the claims.

DESCRIPTION OF THE DRAWINGS

In the accompanying drawings.

Corresponding reference characters indicate corresponding parts throughout the several views of the drawings.

DETAILED DESCRIPTION OF THE INVENTION

Figure 1:
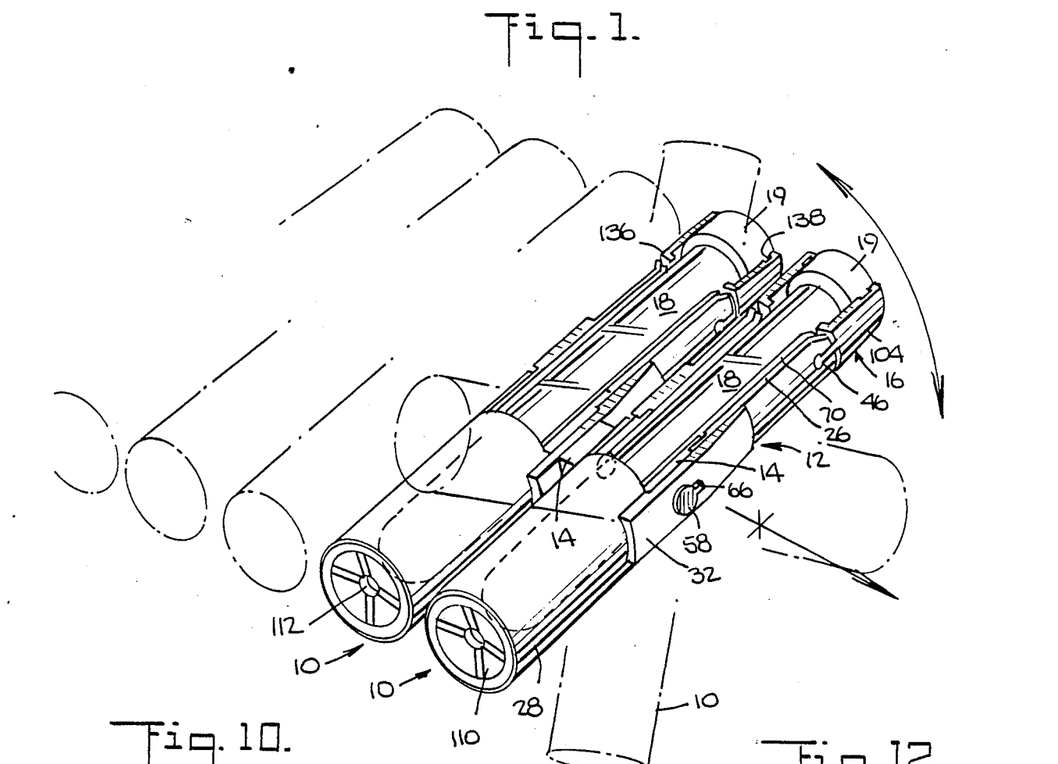
FIG. 1 is a perspective view of a linkage of test tube holders incorporating one embodiment of the invention.
Figure 2:
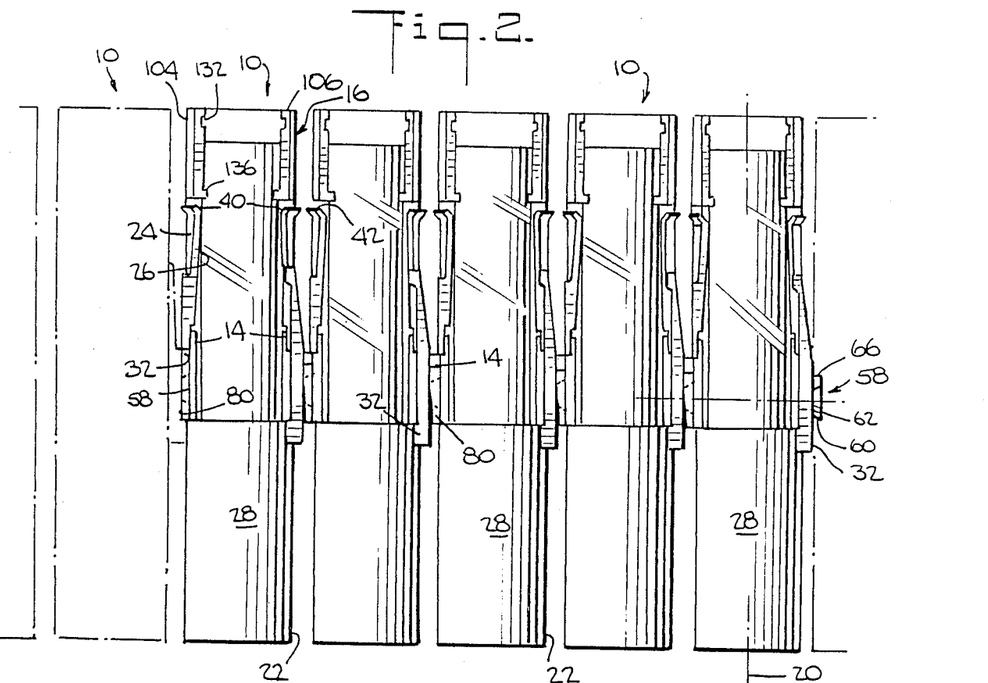
FIG. 2 is a front elevational view thereof.

A test tube holder incorporating one embodiment of the invention is generally indicated by the reference number 10 in FIG. 1.

Unless otherwise indicated, all components of the test tube holder are formed of a durable resilient plastic material such as nylon.

Figures 8, 9, 13:
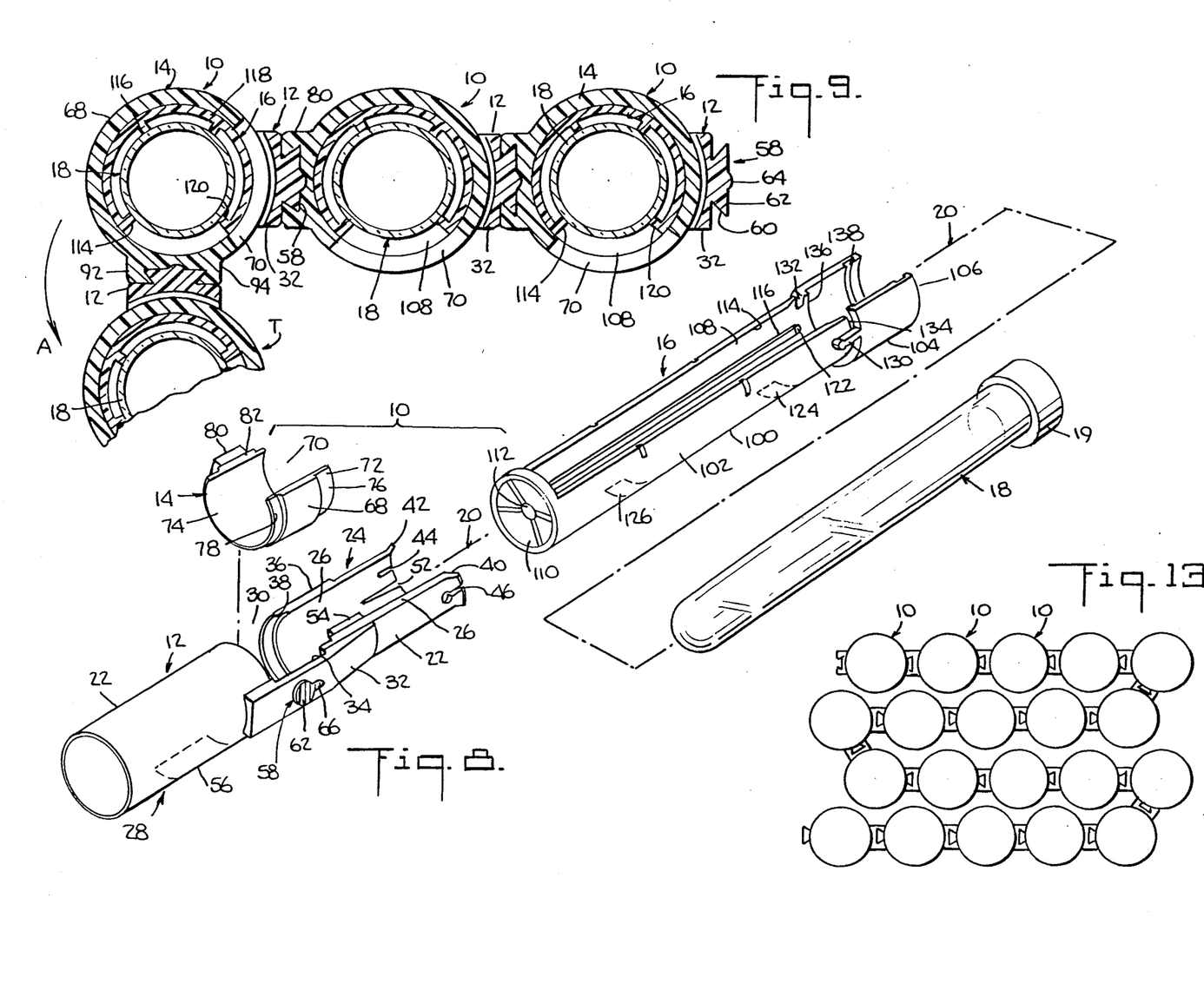
FIG. 8 is an exploded perspective view thereof.
FIG. 9 is a sectional view taken on the line 9—9 of FIG. 6.
FIG. 13 is a simplified end view of the linkage stacked in a fan-fold or Z-fold arrangement.

Referring to FIG. 8, the test tube holder 10 comprises an elongated tubular member 12, a pivot member 14 pivotally supported on the tubular member 12, and an adapter member 16 insertable in the tubular member 12 for accommodating a test tube 18. Preferably the adapter member 18 is formed of a relatively clear material such as polypropylene.

The tubular member 12, which is elongated along a longitudinal axis 20, has a generally cylindrical wall 22 with a split portion 24 having an axial slot 26 formed in the wall 22. The axial slot 26 preferably has a radial extent of at least 90° with respect to the longitudinal axis 20. The tubular member 12 also includes a main body portion 28 and a radial slot 30 formed in the wall 22 intermediate the split portion 24 and the main body portion 28.

The terms "axial" and "radial" as used herein relate to the longitudinal axis 20 as a frame of reference. Thus "axial" refers to a distance or direction parallel to the longitudinal axis 20 and "radial" refers to a distance, direction or location that has a center on the longitudinal axis 20.

The wall portion 22 has a reinforced section 32 which bridges the radial slot 30 to adjoin the main body portion 28 and the split portion 24. An interior recess 34 (FIG. 5), formed in the reinforced section 32, is radially continuous with the radial slot 30.

The split portion 24 has a radially reinforced section 36 (FIG. 8) at the radial slot 30. The reinforced section 36 is formed with an interior radial recess 38 (FIG. 5) that is stepped away from the interior recess 34 toward the longitudinal axis 20. A bevelled lip portion 40 is formed at an open free end 42 of the tubular member 12. The tubular end 42 is also a free end of the split portion 24 and is formed with radially opposite, axially directed key slots 44 and 46. Additional radially spaced, axially directed slots 48, 50 and 52 are also formed at the free end 42.

A window opening 54 is formed in the wall 22 of the split portion 24 radially opposite the axial slot 26. A window opening 56 is formed in the main body portion 28 at the same radial orientation as the window opening 54. However, the window opening 56 is larger than the window opening 54.

Figure 5:
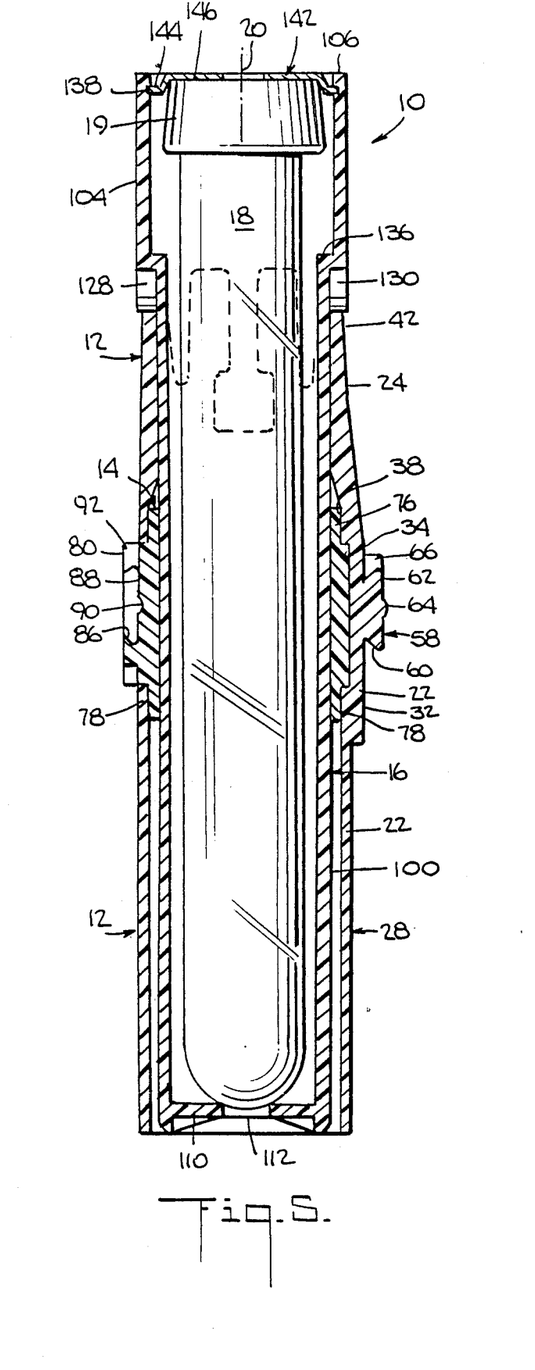
FIG. 5 is a sectional view taken on the line 5—5 of FIG. 4.
Figure 6:
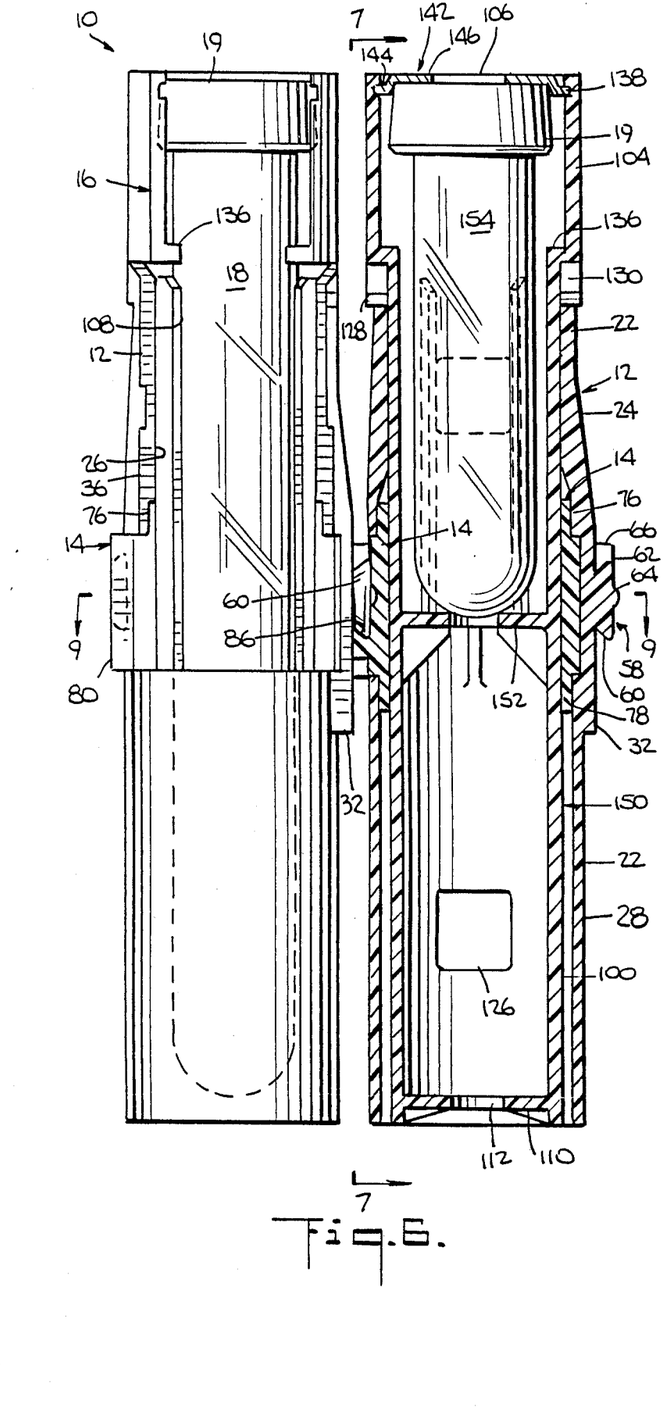
FIG. 6 is an enlarged elevational view thereof, wherein a further embodiment of the invention is incorporated in the linkage.

As seen most clearly from FIGS. 5 and 6, the internal diameter of the main body portion 28 is of greater dimension than the internal diameter of the split portion 24.

A dove-tail latch member 58 (FIG. 5) is formed on the reinforced section 32 and includes a conical surface 60 tapering toward the wall 22 and a base surface 62 with a detent dimple 64. The latch member 58 is oriented approximately 90° away from the median axial element (not shown) of the slot 26. A combination lever portion and stop surface 66 is formed as a stub-like projection that projects radially away from the base 62 and extends axially toward the free end 42 of the tubular member 12.

Figure 10:
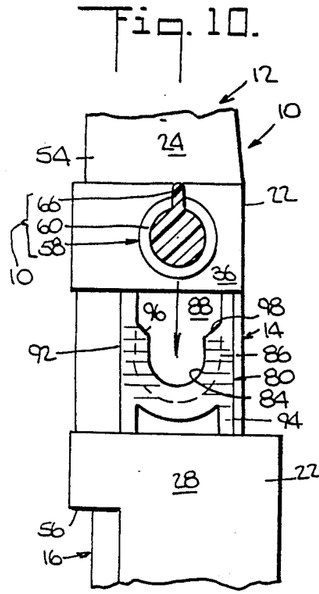
FIG. 10 is an enlarged fragmentary view showing the engagement between latching members of adjacent test tube holders in the linkage.

Referring to FIGS. 8 and 10, the pivot member 14 is in the shape of a collar and includes a generally cylindrical wall portion 68. An axial slot 70 in the wall portion 68 extends through opposite open ends 72 and 74 of the pivot member 14. A pair of axially spaced exterior radial recesses 76 and 78 are formed at the respective opposite ends 72 and 74. The pivot member 14 further includes a latch member 80 formed between the recesses 76 and 78 at an axial edge 82 of the axial slot 70.

The latch member 80 (FIG. 10) comprises a U-shaped latch pocket 84 formed with an inside tapered surface 86 (FIG. 5) that is complementary in shape to the conical surface 60 of the latch member 58. The surface 86 tapers toward a planar surface 88 which includes a small circular detent hollow 90 (FIG. 5). Radially spaced reinforcing leg portions 92 and 94 are formed at opposite sides of the latch member 80 and extend axially from the recess 76 to the recess 78. Inclined stop surfaces 96 and 98 taper from the respective legs 92, 94 to the U-shaped arc of the latch pocket 84.

Referring to FIG. 8, the adapter member 16, which is elongated along the longitudinal axis 20, has a generally cylindrical wall 100 divided into a main body portion 102 and an enlarged collar portion 104 at an open end 106. An axial slot 108 formed in the wall 100 extends from a base end 110 of the main body portion 102 to the open end 106.

Preferably, the axial slot 108 has a radial extent of at least 90° with respect to the longitudinal axis 20. A stabilizer opening 112 is formed in the base end 110. The opening 112 also permits access to a removal tool (not shown) to facilitate removal of the test tube 18 from the test tube holder 10. Elongated radially spaced projecting spines 114, 116, 118 and 120 (FIG. 9) are formed on the interior surface of the main body portion 102. The spines 114, 116, 118 and 120 extend axially from the base end 110 to beveled end portions such as 122 (FIG. 8), located slightly below the collar portion 104.

A pair of aligned, axially spaced window openings 124 and 126 are formed in the wall 100 of the main body portion 102 radially opposite the axial slot 108.

A pair of key projections 128 and 130 (FIG. 5) radially spaced approximately 180° apart extend axially from the collar portion 104 along the exterior wall of the main body portion 102.

Radial slots 132 and 134 (FIG. 8) formed in the wall 100 respectively extend radially from the axial slot 108 to the key projections 128 and 130 to enhance the resilient expansibility of the main body portion 102 with respect to the longitudinal axis 20.

Figure 3:
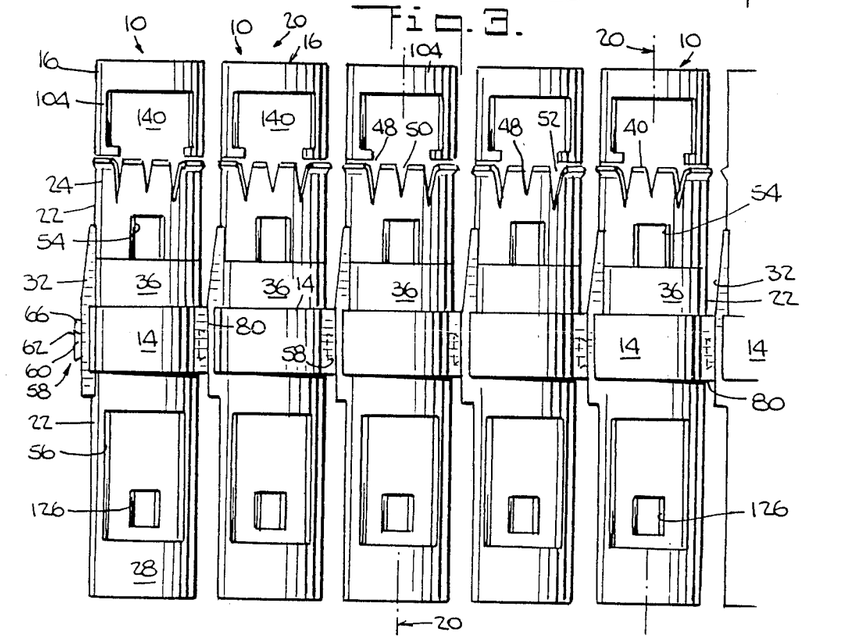
FIG. 3 is a rear elevational view thereof.

The enlarged collar portion 104 is formed with an internal radial ledge 136 where the collar portion 104 meets the main body portion 102. An internal radial groove 138 is formed in the interior surface of the enlarged collar portion 104 near the open end 106. A generally rectangular recess 140 (FIG. 3) is formed in the exterior surface of the collar portion 104 radially opposite the axial slot 108.

In using the test tube holder 10, the pivot member 14 is disposed in the radial slot 30 of the tubular member 12. The pivot member 14 is easily pressed into the slot 30 of the tubular member 12 since the split portion 24 of the tubular member 12 is expandible at the slot 30 to accommodate the pivot member 14. The pivot member 14 is sufficiently compressible at the slot 70 to permit pressing of the pivot member 14 into the desired position.

The pivot member 14 is pivotally supported in the radial slot 30 of the tubular member 12 when the radial recess 76 of the pivot member 14 engages the radial recess 38 of the tubular member 12 at the split portion 24. Similarly, the radial recess 78 of the pivot member 14 engages the interior surface of the main body portion 28 of the tubular member 12.

The pivot member 14 is thus pivotable with respect to the tubular member 12 until either reinforcing leg 92, 94 engages a side of the reinforced section 32 to stop further pivotal movement. It will be noted that because of the pivotal relationship between the pivot member 14 and the tubular member 12, the tubular member 12 is likewise pivotable with respect to the pivot member 14. The actual range of pivotal movement between the pivot member 14 and the tubular member 12 is determined by the radial extent of the reinforced section 32 and the radial spacing between the reinforcing legs 92 and 94. Preferably, the range of pivotal movement is at least 270°.

Figure 7:
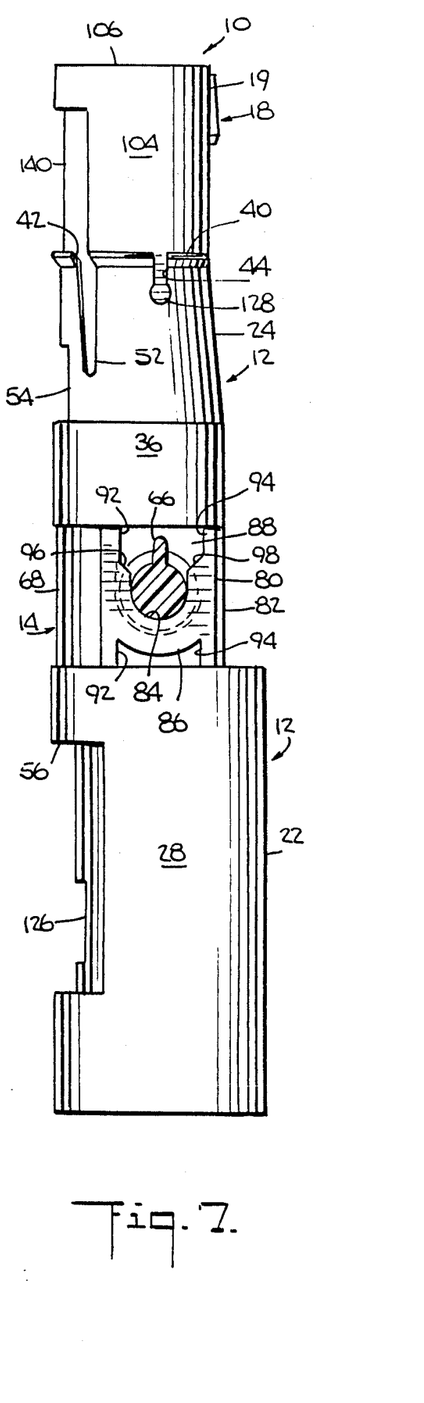
FIG. 7 is a view taken along the line 7—7 of FIG. 6.

Once the pivot member 14 and the tubular member 12 have been assembled, the latch member 58 of one test tube holder 10 can be engaged in the latch member 80 of another test tube holder 10 in the manner shown in FIGS. 10 and 7. Thus, the conical surface 60 of the latch member 58 is received in the latch pocket 84 of the latch member 80. The detent dimple 64 is then engaged in the detent hollow 90 to retain the latch members 58 and 80 together.

It will be noted that the pivot member 14 incorporates the latch member 80. Thus the pivot member 14 along with the latch members 80 and 58 constitute latching means for detachably joining adjacent test tube holders 10 to permit bi-directional radial pivotal movement and bi-directional longitudinal tilting movement.

A continuous linkage of test tube holders 10 can be connected together in this manner to form a linkage of unlimited length.

The relative pivotal relationship between the linked test tube holders affords the linkage with flexibility sufficient to enable the linkage to be stacked in a fanfold or Z-fold arrangement as shown in FIG. 13. A further example of the relative pivotal movement between linked test tube holders is shown in FIG. 9 wherein one of the test tube holders is shown at an angular orientation of approximately 90° with respect to a series of three test tube holders, all of which are joined together in a continuous link. The test tube holder which has been designated by the letter T in FIG. 9 can be further pivoted in the direction A with respect to the adjacent test tube holders 10 until the tubular members 12 of the adjacent test tube holders make contact or the reinforced section 32 of the adjacent test tube holder 10 abuts its own reinforcing legs 94.

It will be noted that the relative pivotal movement between test tube holders is characterized by the longitudinal axis of one test tube holder serving as a center of rotation for another test tube holder.

In addition to relative pivotal movement between test tube holders that have been latched together, there is relative tilting movement such as shown in FIG. 1. The latch connection between adjacent test tube holders, such as shown in FIG. 11, permits one test tube holder 10 to be tilted with respect to another test tube holder 10 in a direction B such that the longitudinal axes of each test tube holder are inclined or skewed with respect to each other.

The maximum tilt angle which can exist between two adjacent connected test tube holders 10 is determined by engagement between the lever portion-stop surface 66 on the latch member 58 with either of the inclined stop surfaces 96, 98 of the latch member 80. An example of such engagement is shown in FIG. 11. It should be noted that one test tube holder alone can be tilted with respect to a series of other test tube holders linked together or several test tube holders can be tilted in unison with respect to several other test tube holders, all of which are connected together in one linkage.

The lever portion-stop surface 66 can also be used to facilitate separation of one test tube holder from another test tube holder. Referring to FIGS. 11 and 12, it will be seen that an attempt to tilt one of the test tube holders 10 in the direction B with respect to the other test tube holder 10, after the lever portion stop surface 66 has engaged the inclined stop surface 98, will cause the lever portion stop surface 66 to exert a force against the inclined stop surface 98.

Figure 11:
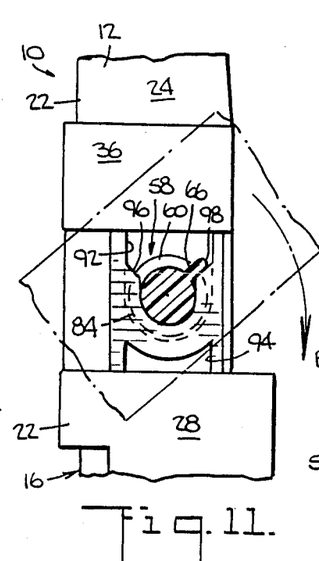
FIG. 11 is an enlarged fragmentary view showing a relative tilted position between adjacent test tube holders in the linkage.
Figure 12:
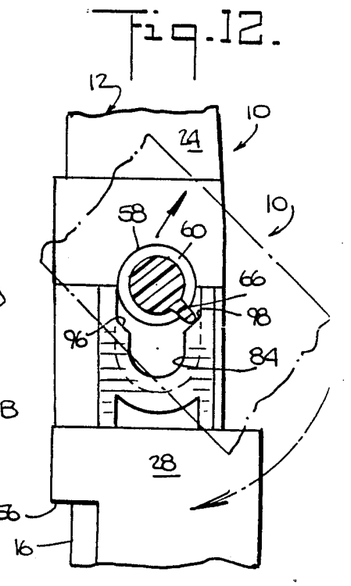
FIG. 12 is an enlarged fragmentary view showing the disengagement of adjacent test tube holders in the linkage.

The stop surface 98, with continued movement of the test tube holder 10 in the direction B as shown in FIG. 11, then functions as a fulcrum whereby the conical surface of the latch member 58 is caused to lift away from the latch pocket 84 in the manner shown in FIG. 12, overcoming the detent between the detent dimple 64 and the detent hollow 90. Once the latch member 58 has separated from the latch member 80 as shown in FIG. 12, the respective test tube holders are separated from each other.

The test tube holder assembly 10 is completed by insertion of the adapter member 16 into the previously assembled tubular member 12 and pivot member 14. However, it should be noted that insertion of the adapter member 16 into the tubular member 12 does not affect the pivoting or tilting relationships previously described for the subassembly of the tubular member 12 and the pivot member 14.

The adapter member 16 is inserted into the free end 42 of the tubular member with the axial slot 108 of the adapter member substantially aligned with the axial slot 26 of the tubular member. This alignment is maintained by engagement of the key projections 128 and 130 on the adapter member in the key slots 44 and 46 at the free end 42 of the tubular member.

Figure 4:
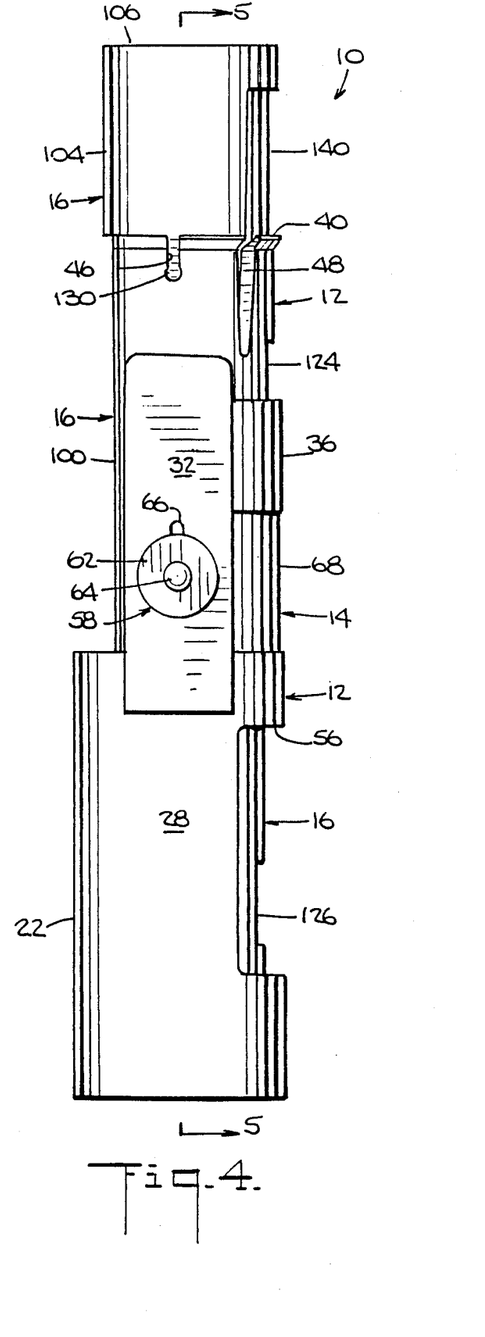
FIG. 4 is an enlarged side elevational view thereof.

Referring to FIG. 4, an enlarged end of the key projection 130, engaged in a correspondingly enlarged end 46 of the key slot, helps detent the adapter member 16 in the tubular member 12.

As shown most clearly in FIG. 5, the tubular member 12 embraces the adapter member 16 primarily at the split portion 24. The main body portion 28 of the tubular member 12 is spaced from the adapter member 16. It will also be noted that the pivot member 14 embraces the adapter member 16 with sufficient clearance to permit relative pivotal movement of the pivot member 14 with respect to the adapter member 16.

The test tube 18 which can be of the type sold under the trade name Vacutainer by Becton Dickinson, is inserted in the adapter member 16, before or after the adapter member 16 has been positioned in the tubular member 12. The test tube 18 is normally sealed with a stopper 19.

Upon insertion of the test tube 18 in the adapter member 16, the test tube periphery engages the projecting spines 114, 116, 118 and 120 as most clearly shown in FIG. 9. The test tube 18 is sized to bottom against the base 110 of the adapter member in the stabilizer opening 112.

Generally the test tube 18 includes a label (not shown) which can be provided with any suitable marking including identification of the individual sample. The test tube 18 is preferably inserted in the adapter member 16 with the label in alignment with the axial slot 108. If desired, the rectangular recess 140 of the adapter member 16 can also be used to accommodate a label.

If desired or if a test tube 18 has been previously opened, a retaining ring 142, such as shown in FIG. 5 can be inserted in the radial groove 138 to enhance retention of the test tube 18 in the adapter member 16 and to enhance retention of the stopper 19 on the test tube 18. The retaining ring 142 includes a flange 144 engagable in the radial groove 138 and an annular portion stepped from the flange 144. The retaining ring 142 is easily inserted into the radial groove 138 since the enlarged collar portion 104 is easily expanded due to the radial slots 132 and 134.

It will be noted that the window portion 124 of the adapter member 16 aligns with the window portion 54 of the tubular member 12 to permit a sensor to check the presence of the test tube 18 in the adapter member 16. The stabilizing opening 112 in the adapter member 16 also facilitates removal of the test tube 18 from the adapter member 16.

Referring to FIG. 6, it will be noted that an adapter member 150 includes an intermediate base portion 152 to accommodate a test tube 154 of shorter axial extent than the test tube 18. The adapter member 150 is in all other respects similar to the adapter member 16 but includes shortened projecting spines (not shown) that correspond to the projecting spines 114, 116, 118 and 120 of the adapter member 16. It will be noted that the retaining ring 142 can be used with either the adapter member 16 or 100 or any other interchangeable adapter which accommodates a different size test tube with a rubber stopper 19.

Thus, adapter members of different size can be interchanged in the test tube holder 10 for accommodating test tubes of different size. The different size test tubes in the respective test tube holders can be incorporated in a single linkage of test tube holders. Thus, the linkage of test tube holders can accommodate test tubes of different size.

It will also be apparent that whether the linkage of test tube holders 10 contain test tubes of one size or another, all such test tube holders can be stacked in the fan-fold arrangement of FIG. 13.

Some advantages of the present invention evident from the foregoing description include a test tube holder that can be connected with other test tube holders to form a linkage of unlimited length. Any of the test tube holders in the linkage can be pivoted with respect to other test tube holders and also tilted with respect to other test tube holders. Thus, one or more of the test tube holders in the linkage can be provided with a movement that is adapted to mixing of the contents of the test tube. A further advantage is that the unlimited length of the linkage enables a continuous uninterrupted feed of test tubes into an analytical apparatus. Thus, fluid samples can be tested on a continuous basis without interruption.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A test tube holder comprising,
   (a) an elongated tubular member, elongated along a longitudinal axis, said tubular member having a first wall portion extending in the direction of said longitudinal axis and a first latch member formed on said first wall portion,
   (b) a pivot member supported on said elongated tubular member to permit relative pivotal movement between said pivot member and said tubular member about said longitudinal axis, said pivot member having a second wall portion extending in the direction of said longitudinal axis and a second latch member formed on said second wall portion such that said first and second latch members are relatively moveable toward and away from each other in a radial direction with reference to said longitudinal axis when there is said relative pivotal movement between said pivot member and said tubular member in opposite directions about said longitudinal axis, and said first and second latch members being respectively arranged on said first and second wall portions such that said first and second latch members are unengagable when said pivot member is supported on said elongated tubular member to permit relative pivotal movement between said pivot member and said tubular member about said longitudinal axis.

2. The test tube holder as claimed in claim 1, wherein said tubular member includes a radial slot formed in said first wall portion, and said pivot member is supported on said tubular member in said radial slot.

3. The test tube holder as claimed in claim 2, wherein said tubular member has an end portion and includes a first axial slot in said first wall portion extending from said radial slot to said end portion.

4. The test tube holder as claimed in claim 3, wherein said tubular member has opposite end portions, and said pivot member has opposite end portions corresponding to the opposite end portions of said tubular member, said pivot member further including a second axial slot in said second wall portion extending to the opposite end portions of said pivot member.

5. The test tube holder as claimed in claim 4 wherein said first and second axial slots are alignable when said first and second latch members are approximately 180° apart.

6. The test tube holder as claimed in claim 1, wherein said pivot member and said tubular member are relatively pivotable through a range of at least 270° with respect to said longitudinal axis to permit relative movement of said first and second latch members through an angle of at least 270°.

7. The test tube holder as claimed in claim 1, wherein said tubular member has a main body portion having a first radius of curvature with respect to said longitudinal axis and said pivot member comprises a collar-like formation having a second radius of curvature that is substantially equivalent in magnitude to the first radius of curvature.

8. The test tube holder as claimed in claim 1, wherein said tubular member has a split portion with a first axial slot of first predetermined axial extent along said longitudinal axis, to provide said tubular member with expandable resilient characteristics in a radial direction with respect to said longitudinal axis along said split portion.

9. The test tube holder as claimed in claim 8, wherein said tubular member includes a main body portion of second predetermined axial extent with respect to said longitudinal axis and a radial slot of third predetermined axial extent with respect to said longitudinal axis, axially intermediate said main body portion and said split portion for accomodating said pivot member for support on said tubular member to permit said relative pivotal movement between said pivot member and said tubular member.

10. The test tube holder as claimed in claim 1, further including an elongated adapter member for accomodating a test tube, said adapter member being insertable in and removeable from said tubular member, and being of complementary curvature with respect to said tubular member, said adapter member being embraced by said pivot member when said adapter member is inserted in said tubular member.

11. The test tube holder as claimed in claim 10, wherein engaging means are provided in said adapter member and said tubular member to locate said adapter member in a predetermined radial orientation with respect to said tubular member when said adapter member is inserted in said tubular member.

12. The test tube holder as claimed in claim 11, wherein said tubular member has a first axial slot in said first wall portion and said pivot member has a second axial slot in said second wall portion alignable with said first axial slot, and said adapter member has a third wall portion with a third axial slot alignable with said first and second axial slots.

13. The test tube holder as claimed in claim 12, wherein said first axial slot is alignable with said third axial slot when the engaging means of said adapter member and said tubular member are engaged.

14. The test tube holder as claimed in claim 13, wherein said second axial slot is alignable with said first and third axial slots when said first and second latch members are approximately 180° apart.

15. The test tube holder as claimed in claim 10, wherein said pivot member and said tubular member are relatively pivotable through a range of at least 270° with respect to said longitudinal axis to permit relative movement of said first and second latch members through an angle of at least 270°, and wherein a plurality of said test tube holders are latchable together in consecutive fashion at respective said first and second latch members to form a continuous linkage of said plurality of test tube holders, said pivotal range of movement between each said pivot member and each said tubular member of said continuous linkage of test tube holders permitting a fan-fold arrangement of said continuous linkage of test tube holders.

16. The test tube holder as claimed in claim 15, wherein the respective said first and second latch members are structured to form a pivot joint such that the respective test tube holders of said continuous linkage of test tube holders are further moveable with respect to each other in a manner whereby the longitudinal axis of any of said test tube holders can be tilted about said pivot joint in a skewed relationship with respect to the longitudinal axis of any of the other said test tube holders in said continuous linkage of said test tube holders.

17. The test tube holder as claimed in claim 11, wherein said adapter member includes a third wall portion with a first window opening for communication with a sensing device.

18. The test tube holder as claimed in claim 17, wherein said adapter member includes a second window opening in said third wall accessible to facilitate removal of said test tube from said adapter member.

19. The test tube holder as claimed in claim 18, wherein said tubular member includes third and fourth window openings in said first wall respectively alignable with said first and second window openings when the engaging means of said adapter member and said tubular member are aligned.

20. The test tube holder as claimed in claim 10, wherein said adapter member includes a test tube receptacle portion of a first predetermined size for accomodating a first said test tube corresponding to said first predetermined size.

21. The test tube holder as claimed in claim 20, wherein said adapter member is interchangeable with another said adapter member having a test tube receptacle portion of a second predetermined size for accomodating a second said test tube corresponding to said second predetermined size.

22. The test tube holder as claimed in claim 10, wherein said adapter member includes a third wall portion with an axial slot of predetermined axial extent along said longitudinal axis to provide said adapter member with expandable resilient characteristics in a radial direction with respect to said longitudinal axis, along said axial slot.

23. The test tube holder as claimed in claim 22, wherein said adapter member includes an inside surface of said third wall portion and projecting means formed on said inside surface for engagement with the surface of a test tube.

24. The test tube holder as claimed in claim 1, wherein the first latch member of a first said test tube holder is engagable with the second latch member of a second said test tube holder to link said first and said second test tube holders together such that said first and said second test tube holders are movable with respect to each other in a manner whereby the longitudinal axis of said first test tube holder is an axis of rotation for said second test tube holder.

25. The test tube holder as claimed in claim 24, wherein said pivot member and said tubular member are relatively pivotable through a range of at least 270° with respect to said longitudinal axis to permit relative movement of said first and second latch members through an angle of at least 270°, and wherein a plurality of said test tube holders are latchable together in consecutive fashion at respective said first and second latch members to form a continuous linkage of said plurality of test tube holders, said pivotal range of movement between each said pivot member and each tubular member of said continuous linkage of test tube holders permitting a fan-fold arrangement of said continuous linkage of test tube holders.

26. The test tube holder as claimed in claim 24, wherein the first latch member of said first test tube holder and the second latch member of said second test tube holder are structured to form a pivot joint such that said first and said second test tube holders, when linked by latchable engagement of the respective said first and second latch members, are further moveable with respect to each other in a manner whereby the longitudinal axis of said first test tube holder is tiltable about said pivot joint in a skewed relationship with respect to the longitudinal axis of said second test tube holder.

27. The test tube holder as claimed in claim 26, wherein one of the engagable latch members of said first and second test tube holders includes a lever portion and the other engagable latch member of said first and second test tube holders includes a lever engaging portion such that a predetermined tilting movement of said first latch member of said first test tube holder with respect to said second latch member of said second test tube holder when said first and second test tube holders are linked together will cause said lever portion to bear against said lever engaging portion to disengage said first test tube holder from said second test tube holder.

28. The test tube holder as claimed in claim 24, wherein said first latch member of said first test tube holder and second latch member of said second test tube holder are formed with detent means for maintaining the link connection between said first and said second test tube holders.

29. The test tube holder as claimed in claim 24, wherein the first latch member of the first test tube holder and the second latch member of the second test tube holder form a dove-tail joint when engaged to link together said first and said second test tube holders.

30. The test tube holder as claimed in claim 29, wherein a male portion of said dove-tail joint is formed on said tubular member and a female portion of said dove-tail joint is formed on said pivot member.

31. A linkage of test tube holders comprising,
(a) at least two elongated tubular members, elongated along respective longitudinal axes, and having respective first latch members formed thereon,
(b) at least two pivot members respectively pivotally supported on the respective elongated tubular members to define two respective sets, each said set having relative pivotal movement between the pivot members and the respective tubular members about the respective longitudinal axes, the pivot members of each set having respective second latch members formed thereon, the first and second latch members of each said set being relatively moveable toward and away from each other in a radial direction with reference to the respective longitudinal axes when there is said relative pivotal movement in each said set between said pivot member and said tubular member in opposite directions about the respective longitudinal axes, the first latch member of one said set being latched with the second latch member of the other said set whereby the longitudinal axis of said one set is an axis of rotation for the other said set.

32. The linkage as claimed in claim 31, wherein the first and second latch members of each said set are structured to form a pivot joint such that one said set is further moveable with respect to the other said set in a manner whereby the longitudinal axis of said one set can be tilted about said pivot joint in a skewed relationship with respect to the longitudinal axis of the other said set.

33. The linkage as claimed in claim 32, further including an elongated adapter member for accommodating a test tube insertable in and removeable from the tubular member of each said set.

34. A linkage comprising
(a) a plurality of elongated test tube holders with respective longitudinal axes, detachably joined together to form a continuous linkage,
(b) latching means for detachably joining the test tube holders together to permit a first bi-directional pivot movement between said test tube holders such that the longitudinal axis of one test tube holder is an axis of rotation for an adjacent test tube holder, and
(c) said latching means further including a pivot joint between adjacent test tube holders for permitting a second bi-directional pivotal movement between said adjacent test tube holders such that one of said adjacent test tube holders can be tilted about said pivot joint with respect to the other said adjacent test tube holder whereby the longitudinal axis of said one adjacent test tube holder is inclinable in opposite directions with respect to the longitudinal axis of the other adjacent test tube holder.

35. The linkage of claim 34 wherein said test tube holders comprise an elongated tubular member and said latching means include a pivot member pivotally supported on said elongated tubular member for relative radial movement with respect to said tubular member about said longitudinal axis.

36. The linkage of claim 35 wherein said latching means further comprise a first latch member on said elongated tubular member and a second latch member on said pivot member.

37. The linkage of claim 36 wherein said first latch member of said one adjacent test tube holder is engagable with the second latch member of the other adjacent test tube holder to form said pivot joint.

38. The linkage as claimed in claim 37 wherein said latching means include means for facilitating release of the latch connection between said first and second latch members of said adjacent test tube holders.

* * * * *